(12) United States Patent
Terruzzi et al.

(10) Patent No.: US 9,642,834 B2
(45) Date of Patent: May 9, 2017

(54) COMPOSITION COMPRISING ALPHA-LIPOIC ACID AND HONOKIOL FOR TREATING NEUROPATHIES

(71) Applicant: Giellepi S.p.A., Milan MI (IT)

(72) Inventors: Carlo Terruzzi, Briosco MB (IT); Fabio Terruzzi, Briosco MB (IT)

(73) Assignee: GIELLEPI S.P.A., Milan (MI) (IT)

( * ) Notice: Subject to any disclaimer, the term of this patent is extended or adjusted under 35 U.S.C. 154(b) by 0 days.

(21) Appl. No.: 14/395,265

(22) PCT Filed: Apr. 19, 2013

(86) PCT No.: PCT/IB2013/053102
§ 371 (c)(1),
(2) Date: Oct. 17, 2014

(87) PCT Pub. No.: WO2013/156971
PCT Pub. Date: Oct. 24, 2013

(65) Prior Publication Data
US 2015/0093454 A1 Apr. 2, 2015

(30) Foreign Application Priority Data
Apr. 20, 2012 (IT) .............................. MI2012A0661

(51) Int. Cl.
*A61K 31/385* (2006.01)
*A61K 31/05* (2006.01)
*A23L 33/10* (2016.01)
*A23L 33/12* (2016.01)

(52) U.S. Cl.
CPC ............ *A61K 31/385* (2013.01); *A23L 33/10* (2016.08); *A23L 33/12* (2016.08); *A61K 31/05* (2013.01); *A23V 2002/00* (2013.01)

(58) Field of Classification Search
CPC .. A61K 2300/00; A61K 31/05; A61K 31/385; A23V 2002/00; A23L 33/10; A23L 33/12
See application file for complete search history.

(56) References Cited

U.S. PATENT DOCUMENTS

| | | | |
|---|---|---|---|
| 7,776,915 B2* | 8/2010 | Morariu | A61K 8/41 424/401 |
| 2006/0018975 A1* | 1/2006 | Talbott | A61K 31/375 424/646 |
| 2006/0216251 A1* | 9/2006 | Morariu | A61K 8/41 424/59 |
| 2010/0272790 A1* | 10/2010 | Morariu | A61K 8/41 424/450 |
| 2015/0209306 A1* | 7/2015 | Bredesen | A23L 1/302 424/94.1 |

OTHER PUBLICATIONS

Ziegler, D., et al., Oral Treatment With [Alpha]-Lipoic Acid Improves . . . , Diabetes Care, vol. 29, No. 11, pp. 2365-2370, 2006.
Yoshiyasu, F., Neurotrophic Activity of Honokiol . . . , Bioorganic & Medicinal Chemistry Letters, vol. 12, No. 8, pp. 1163-1166, 2002.
Lee, Young-Jung, et al., Therapeutic Applications of Compounds in the Magnolia Family, Pharmacology & Therapeutics, vol. 130, No. 2, pp. 157-176, 2011.
International Search Report issued in PCT Application No. PCT/IB2013/053102.
Written Opinion of International Searching Authority issued in counterpart PCT Application No. PCT/IB2013/053102.
English Translation of Notice on the First Office Action issued by the State Intellectual Property Office of the People's Republic of China on Oct. 9, 2015 in connection with the related Chinese Patent Application No. 201380020986.2 (4 pages).
First Office Action issued by the State Intellectual Property Office of the People's Republic of China on Oct. 9, 2015 in connection with the related Chinese Patent Application No. 201380020986.2 (in Chinese) (3 pages).

* cited by examiner

*Primary Examiner* — Robert A Wax
*Assistant Examiner* — Olga V Tcherkasskaya
(74) *Attorney, Agent, or Firm* — Lucas & Mercanti, LLP

(57) ABSTRACT

The present invention relates to a composition comprising alfa-lipoic acid, or a salt or complex thereof, and honokiol, wherein the weight quantity of said honokiol is between 1% and 30% with respect to the total weight of honokiol and alfa-lipoic acid.

13 Claims, 2 Drawing Sheets

COMPOSITION COMPRISING ALPHA-LIPOIC ACID AND HONOKIOL FOR TREATING NEUROPATHIES

CROSS-REFERENCE TO RELATED APPLICATIONS

This application is a 371 of PCT/IB2013/053102, filed Apr. 19, 2013, which claims the benefit of Italian Patent Application No. MI2012A000661, filed Apr. 20, 2012, the contents of each of which are incorporated herein by reference.

FIELD OF THE INVENTION

The present invention relates to a composition for the treatment of neuropathies, and in particular a composition for the treatment of painful sensory syndromes of peripheral neuropathy.

BACKGROUND OF THE INVENTION

Numerous compositions useful for administration to persons suffering from neuropathies are known.

In particular, it is known that compositions comprising alpha-lipoic acid have a beneficial effect in the treatment of neuropathies, particularly of acquired peripheral neuropathies. As a matter of fact, alpha-lipoic acid improves the antioxidant barrier and reduces oxidative stress by increasing the levels of glutathione, improves the speed of nerve communication, thus optimizing its functionality, and finally exerts normalizing action against nervous sensitivity, thus reducing both pain and sensory turbidity.

Recent in vivo studies have confirmed the neuroprotective and cardioprotective effects of alpha-lipoic acid.

Quick- or conventional-release compositions comprising dietary alpha-lipoic acid for a single daily administration of 300 mg or 600 mg of alpha-lipoic acid are known.

Published studies "Oral Treatment With α-Lipoic Acid Improves Symptomatic Diabetic Polyneuropathy—The SYDNEY 2 trial" Dan Ziegler et. al., Diabetes Care November 2006 vol. 29 no. 11, p. 2365-2370, and "Thioctic Acid and Acetyl-L-Carnitine in the Treatment of Sciatic Pain Caused by a Herniated Disc" Memeo Antonio and Mario Loiero, Clin. Drug Investigation 2008, Vol. 28, p 495-500, report that a daily dose of 600 mg of alpha-lipoic acid provides the best risk/benefit ratio for the treatment of symptoms of diabetic polyneuropathy and sciatic pain. According to the first study, compared to a daily dose of 600 mg, the higher doses of 1200 mg and 1800 mg do not provide a better response in terms of improvement in the symptoms of diabetic polyneuropathy. The study also shows a dose-dependent increase of the side effects related to alpha-lipoic acid, such as nausea, vomiting and dizziness.

It is also known that the bark of *Magnolia*, a phytoderivative obtained from *Magnolia Officinalis*, belonging to the family of Magnoliacee, contains two phenolic compounds, honokiol and magnolol. A number of pharmacological properties, such as anti-anxiety, anti-inflammatory, antimicrobial, antioxidant, antiplatelet and neurotrophic properties are ascribed to *Magnolia* bark.

Y. Fukuyama, Nakade K., Minoshima Y., Yokoyama, A., H. Zhai, Y. Mitsumoto "Neurotrophic activity of honokiol on the cultures of fetal rat cortical neurons," Bioorg. Med Chem. Lett 2002 Apr. 22; 12 (8):1163-6 describes neurotrophic activities of honokiol at concentrations between 0.1 and 10 μM on cultured rat cortical neurons. In cortical neurons, honokiol is able to promote neurite growth. Furthermore, honokiol has proved capable of increasing the survival and development of neurons of primary cultures.

As regards the neurotrophic activity of honokiol, Lee Y J. et al. "Therapeutic applications of compounds in the *magnolia* family," Pharmacol. Ther. 2011, 130 (2): 157-76 describes effective doses in rats ranging from 0.01 g/kg and 0.25 g/kg. There is no known study that shows an effective dosage for humans.

US2006251608 describes formulations for the treatment of aged skin, comprising antioxidants, co-promoters of anti-oxidation, anti-inflammatory agents, vitamins, minerals and promoters of collagen synthesis. It is not mentioned any effectiveness of such formulations for the treatment of neuropathies. Alpha-lipoic acid and honokiol are both mentioned as possible antioxidants in such formulations, but a combination of such compounds is not specifically described.

Nutritional supplements for athletes are known, useful for improving muscle mass, strength and physical strength which include, among many other components, also alpha-lipoic acid and *magnolia* bark containing 2% honokiol. An effect of these supplements for the treatment of neuropathies is not reported, and the amount of honokiol in such supplements is extremely reduced. In particular, the ratio of honokiol and alpha-lipoic acid in such supplements known turns out to be less than 0.3%.

SUMMARY OF THE INVENTION

The object of the present invention is therefore to provide a composition comprising alpha-lipoic acid and having an improved activity in the treatment of symptoms and neuropathic pain. Said object is achieved with a composition, and a pharmaceutical or dietary formulation in accordance with the present invention described herein. Other features of the composition and the formulation according to the present invention are described below.

DETAILED DESCRIPTION OF THE INVENTION

The composition according to the present invention comprises alpha-lipoic acid, or a salt or complex thereof, and honokiol, and is characterized by the fact that the amount by weight of honokiol is between 1% and 30% with respect to the total weight of the two components honokiol and alpha-lipoic acid.

The alpha-lipoic acid contained in the composition according to the present invention may be in racemic form, i.e. it may be a mixture of the two enantiomeric forms R and S, and/or salts or complexes thereof, or the composition according to the present invention may comprise only the biologically active R enantiomeric form, or a salt or complex thereof.

As a matter of fact, the inventors have surprisingly found that the efficacy of alpha-lipoic acid in the treatment of neuropathies and pain syndromes associated therewith is enhanced when said alpha-lipoic acid is associated with honokiol in certain proportions, because of a synergy effect.

In particular, the studies conducted by the inventors have shown that in primary cultures of neurons, administration of compositions of alpha-lipoic acid and honokiol according to the invention is effective in promoting neurite extension and cell survival, whereas a similar administration of compositions comprising alpha-lipoic acid and honokiol in an amount from 0 to less than 1% is not significantly effective in promoting the extension of neurites.

Preferably, the amount by weight of honokiol in the composition according to the present invention is between 2% and 15%, more preferably between 3% and 10% with respect to the total weight of honokiol and alpha-lipoic acid.

Indeed, it was found that the above listed ranges are the optimum ratios between the concentrations of alpha-lipoic acid and honokiol, and in these ratios the two active substances have a clear synergistic effect as evidenced by the comparison of the significant activity of the association with the activity of alpha-lipoic acid and of honokiol, when used alone.

As salts or complexes of alpha-lipoic acid, for example water-soluble salts such as sodium or potassium R-lipoate, and other soluble salts of the R enanthiomer or of the RS-racemate can be used in the composition according to the present invention.

The composition according to the present invention preferably further comprises other active principles which form, in combination with alpha-lipoic acid or a salt or complex thereof and honokiol, a particularly effective composition for the treatment of non-diabetic and peripheral neuropathies.

Preferably, the composition according to the present invention therefore comprises gamma-linolenic acid or a salt or complex, for example the sodium salt of gamma-linolenic acid. Preferably, the amount by weight of said gamma-linolenic acid in the composition according to the present invention is between 2% and 30% with respect to the total weight of honokiol and alpha-lipoic acid. More preferably, the amount by weight of said gamma-linolenic acid in the composition according to the present invention is between 15% and 25% compared to the total weight of honokiol and alpha-lipoic acid.

The composition according to the present invention preferably also comprises a physiologically acceptable source of selenium. By physiologically acceptable source of selenium, in the present description and in the claims it is meant any source of assimilable selenium, usable in dietary or pharmaceutical compositions, for example a salt of selenium or selenium complexed with an amino acid. Preferably, a compound selected from the group consisting of selenomethionine, sodium selenite, sodium selenate and selenium yeast is used as physiologically acceptable source of selenium.

Preferably, the amount by weight of said physiologically acceptable source of selenium in the composition according to the present invention is suitable to provide a quantity of selenium between 0.0001% and 2% with respect to the total weight of honokiol and alpha-lipoic acid. More preferably, the amount by weight of said physiologically acceptable source of selenium in the composition according to the present invention is suitable to provide a quantity of selenium between 0.0001% and 0.1% with respect to the total weight of honokiol and alpha acid-lipoic acid.

The composition according to the present invention preferably comprises also at least one component selected from the group formed by vitamin C, vitamin E and B group vitamins, for example vitamins B1, B2, B5, B6 and B12.

The composition according to the invention may be formulated in any suitable form for oral administration. In particular, in one aspect, the invention relates to a dietary or pharmaceutical formulation for oral administration, comprising a composition as defined above, in the form of a pill, tablet, capsule, chewable tablet, chewing gum, pellets, powder for oral suspension, granular powder to be reconstituted or buccal powder, oral suspension, syrup.

The composition according to the present invention may also comprise excipients, fragrances and other substances approved for food use according the type of desired pharmaceutical formulation. Suitable excipients for the production of tablets or capsules are, for example, potato, wheat or corn starch, partially pregelatinized starch, microcrystalline cellulose, dibasic calcium phosphate, calcium carbonate, polyols such as mannitol and sorbitol, maltodextrin, lactose, colloidal silica, highly dispersed silicon dioxide, glyceryl behenate, propylene glycol, polyvinylpyrrolidone, cross-linked polyvinylpyrrolidone, esters and ethers of cellulose (eg, carboxymethylcellulose, hydroxypropylmethyl cellulose, hydroxypropyl cellulose), cross caramellose sodium, alginates, carrageenans, magnesium stearate, sodium stearyl fumarate, titanium dioxide, gelatin, vegetable oils such as soybean or sunflower oil, poliglicerol oleate, glycerol, triglycerides of fatty acids, lecithin.

Preferably, the formulation according to the invention is in the form of tablets or capsules suitable for the daily administration of a quantity of alpha-lipoic acid of from 200 mg to 1300 mg, and of a quantity of honokiol of from 2.5 mg to 150 mg.

More preferably, the formulation according to the invention is in the form of tablets or capsules suitable for the daily administration of an amount of 580 mg to 620 mg of alpha-lipoic acid and an amount of from 45 mg to 60 mg of honokiol, or suitable to daily administration of an amount of from 280 mg to 320 mg of alpha-lipoic acid and from 20 mg to 30 mg of honokiol.

Even more preferably, the formulation according to the invention is in the form of tablets or capsules suitable for the daily administration of an amount of 600 mg of alpha-lipoic acid and of a quantity of 54 mg of honokiol, or suited to daily administration of an amount of 300 mg of alpha-lipoic acid and 27 mg of honokiol.

With the expression "suitable for the daily administration of", in the present description and in the claims it is meant that each capsule or tablet contains either the total quantities of active ingredients specified or fractions of the same quantities such as to allow the administration of the overall quantity through more capsules or tablets. For example, capsules or tablets containing about 300 mg of alpha-lipoic acid and 15 mg of honokiol are considered suitable for the daily administration of about 600 mg of alpha-lipoic acid and 30 mg of honokiol.

The gamma linolenic acid or salt or complex thereof are contained in the formulation according to the present invention in amounts ranging between 10 mg and 300 mg.

A preferred formulation according to the invention is suitable for the daily administration of an amount of from 580 mg to 620 mg of alpha-lipoic acid, an amount of from 45 mg to 60 mg of honokiol and an amount of from 125 mg to 140 mg of gamma-linolenic acid and is in the form of soft capsules of gelatin. Another preferred formulation according to the invention, in the form of soft capsules of gelatin, is suitable for the daily administration of an amount of from 280 mg to 320 mg of alpha-lipoic acid, of an amount of from 20 mg to 30 mg of honokiol and of an amount of from 60 mg to 70 mg of gamma-linolenic acid.

The already described physiologically acceptable source of selenium is contained in the formulation according to the present invention in an amount such as to provide a quantity of selenium between 1 μg and 90 μg.

Vitamin C is preferably included in the formulation according to the present invention in an amount comprised between 20 mg and 1000 mg.

Vitamin E is preferably included in the formulation according to the present invention in an amount between 1 mg and 100 mg Vitamin B1 is preferably included in the formulation according to the present invention in an amount between 1 mg and 5 mg.

Vitamin B2 is preferably included in the formulation according to the present invention in an amount between 1 mg and 5 mg.

Vitamin B5 is preferably included in the formulation according to the present invention in an amount between 1 mg and 20 mg Vitamin B6 is preferably included in the formulation according to the present invention in an amount between 1 mg and 8 mg Vitamin B12 is preferably included in the formulation according to the present invention in an amount ranging between 0.001 mg and 0.020 mg.

A preferred formulation according to the invention comprises about 600 mg of alpha-lipoic acid, approximately 54 mg of honokiol, about 140 mg of gamma-linolenic acid and about 0.110 mg of sodium selenite.

Another preferred formulation according to the invention comprises about 300 mg of alpha-lipoic acid, approximately 27 mg of honokiol, and about 66 mg of gamma-linolenic acid and about 0.055 mg of sodium selenite.

The technique of preparation of the composition according to the present invention is selected depending on the type of administration and other practical considerations.

For the preparation of the formulations according to the present invention, any technique that is known to those skilled in the art for the production of tablets with a low melting active ingredient may be used, for example direct compression after mixing of powders, wet or dry compression after granulation (for example in fluid bed), compression of granules or pellets. The production of capsules may be carried out for example by filling of preformed shells (body) with powders, granules, small tablets or pellets and subsequent closure by applying a head; by forming possibly colored sheets of gelatin wherein a suitable plasticizer is incorporated, and contemporary filling them with liquids (eg Sherer method) or solids (eg Accogel method); by dripping gelatin with plasticizer and possibly the actives, in cold oily solutions (eg dripping method).

BRIEF DESCRIPTION OF THE DRAWINGS

The advantages of the compositions and formulations according to the present invention will become apparent to those skilled in the art from the following examples, with reference to the accompanying drawings in which.

EXAMPLES

Materials and Methods

Figure 1:
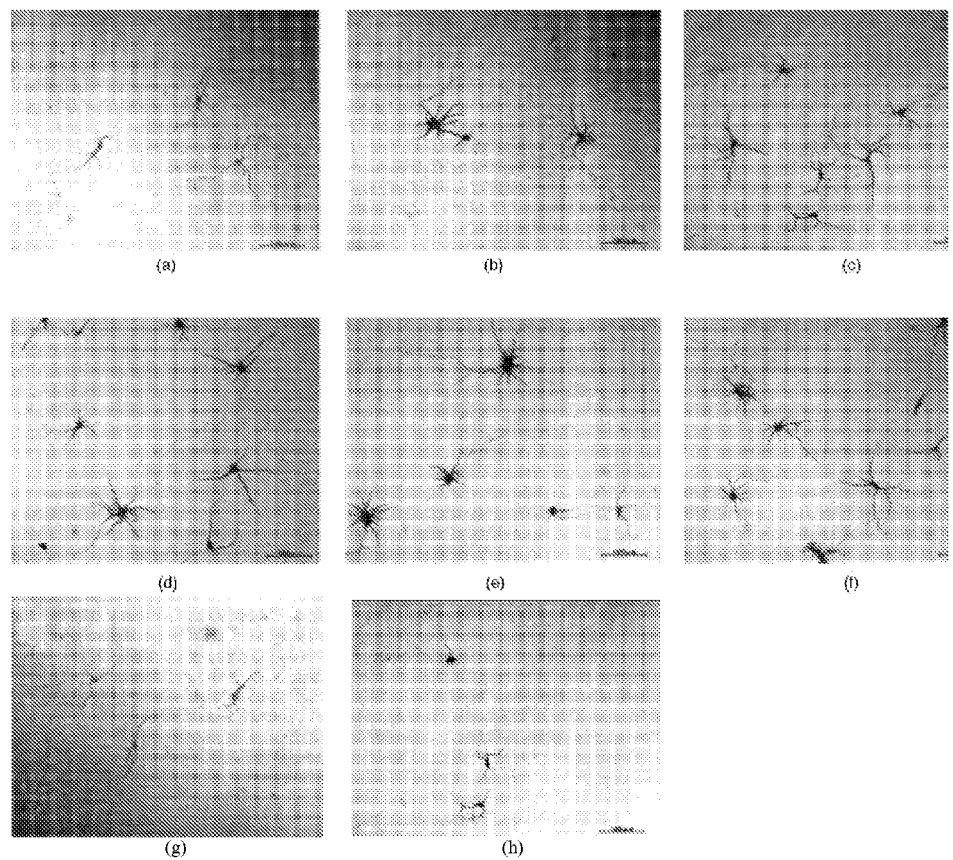
FIG. 1a shows a photograph of a primary cell culture of rat cortical neurons after 7 days in 0.5% EtOH.
FIG. 1b shows a photograph of a primary cell culture of rat cortical neurons after 7 days in 0.5% EtOH additioned with 40 ng ml-1 bFGF.
FIG. 1c shows a photograph of a primary cell culture of rat cortical neurons after 7 days in 0.5% EtOH additioned with a 10 µM solution of 99.7% alpha-lipoic acid and 0.3% honokiol.
FIG. 1d shows a photograph of a primary cell culture of rat cortical neurons after 7 days in 0.5% EtOH additioned with a 10 µM solution of 95.5% alpha-lipoic acid and 4.5% honokiol.
FIG. 1e shows a photograph of a primary cell culture of rat cortical neurons after 7 days in 0.5% EtOH additioned with a 10 µM solution of 91% alpha-lipoic acid and 9% honokiol.
FIG. 1f shows a photograph of a primary cell culture of rat cortical neurons after 7 days in 0.5% EtOH additioned with a 10 µM solution of 46% alpha-lipoic acid and 54% honokiol.
FIG. 1g shows a photograph of a primary cell culture of rat cortical neurons after 7 days of 0.5% EtOH additioned with a 10 µM solution of alpha-lipoic acid alone.
FIG. 1h shows a photograph of a primary cell culture of rat cortical neurons after 7 days of 0.5% EtOH additioned with a 10 µM solution of honokiol alone.

The purity of the used compounds was verified by high performance liquid chromatography (HPLC, single peak), by nuclear magnetic resonance ($H^1$) and ($C^{13}$) and by high resolution mass spectrometry.

The culture medium was Dulbecco's modified culture medium (DMEM), fetal bovine serum (FBS) and B27 supplement were obtained from Gibco BRL (NY, USA). The reagents PD98059 [2-(2-amino-3-methoxyphenyl)-4H-1-benzopyran-4-one], LY294002 [2-(4-morpholinyl)-8-phenyl-1(4H)-benzopyran-4one], and KN93 [N-[2-[N-(4-chlorocinnamyl)-N-methylaminomethyl]phenyl]-N-(2-hydroxyethyl)-4-methoxybenzenesulfonamide phosphate salt] were purchased from Sigma (MO, USA). Human recombinant fibroblast growth factors (bFGF) were supplied by Upstate Biotechnology Inc. (NY, USA). All other used reagents are reagents of highest purity available on the market.

Example 1

Morphological

Eight primary cellular cultures were prepared as described in Abe K et al. "*Effects of recombinant human basic fibroblast growth factor and its modified protein CS23 on survival of primary cultured neurons from various regions of fetal rat brain.*", Jpn J Pharmacol 1990, 53 (2): 221-7. All operations were carried out under sterile conditions.

Neuronal cells were separated from cerebral hemispheres of rat fetuses of 18 days (Japan SLC, Inc.) and suspended in 10% FBS/MEM, then seeded at 9000 cells $cm^{-2}$ in poly-L-lysine plates.

After 24 hours, the culture medium was replaced with a serum-free medium, specific for the growth of neurons (Neurobasal Medium) supplemented with B27.

Then, a first culture (A) was used as the control culture.

A second culture (B) was additioned with 40 ng mL$^{-1}$ of bFGF.

A third culture (C) was additioned with 99.7% by weight alpha-lipoic acid and 0.3% by weight honokiol to the overall concentration of 10 µM.

A fourth culture (D) was additioned with 95.5% by weight alpha-lipoic acid and 4.5% by weight honokiol to the overall concentration of 10 µM.

A fifth culture (E) was additioned with 91% by weight alpha-lipoic acid and 9% by weight honokiol to the overall concentration of 10 µM.

A sixth culture (F) was additioned with 46% by weight alpha-lipoic acid and 54% by weight honokiol to the overall concentration of 10 µM.

A seventh culture (G) was additioned with only alpha-lipoic acid to the overall concentration of 10 µM.

An eighth culture (H) was additioned with only honokiol to the overall concentration of 10 µM.

After 6 days incubation, the cells of the eight cultures were fixed with 4% formaldehyde.

The eight cultures were then evaluated regarding the length of neurites at the microscopic level. The neurons were subjected to immunohistochemical staining for the microtubule-associated protein-2 (MAP2) according to the histochemical method for the length of neurites, as described in Fukuyama Y et al. "*Neurotrophic activity of honokiol on the cultures of fetal rat cortical neurons*" Bioorg. Med Chem. Lett 12, 1163-66 (2002). The length of the most extended neurite of the whole cellular body was measured and calculated by using software programs Lumina Vision and Mac-SCOPE, according to the above-mentioned method described in Y. Fukuyama et al. (2002). The morphometric analyses were performed by measuring the length of the longest neurite from each neuron using Lumina Vision and Mac-Scope software (Yoshiyasu Fukuyama et al. 2002).

The results are shown in Table 1, in which p denotes statistical significance and ns means "not significant".

TABLE 1

| Culture | ALA/honokiol ratio | Increase of average neurite length (µm) | Increase respect to control (culture A) |
|---|---|---|---|
| A | — | 280 | 1 |
| B | — | 295 (p = ns) | 1.05 |
| C | ALA (99.7%) honokiol (0.3%) | 450 (p = ns) | 1.61 |
| D | ALA (95.5%) honokiol (4.5%) | 585.4 (p < 0.001) | 2.09 |
| E | ALA (91%) honokiol (9%) | 630.7 (p < 0.001) | 2.25 |
| F | ALA (46%) honokiol (54%) | 289 (p = ns) | 1.03 |
| G | ALA (100%) | 285 (p = ns) | 1.01 |
| H | honokiol (100%) | 287 (p = ns) | 1.02 |

The length of neurites in cultures treated with the tested compositions according to the invention, with a concentration of honokiol between 4.5% and 9%, resulted significantly increased (p<0.001), while cultures treated with a composition containing alpha-lipoic acid 99.7% and 0.3% honokiol did not show a statistically significant increase in the length of neurites. The composition comprising 95.5% by weight alpha-lipoic acid and 4.5% by weight honokiol, and the one comprising 91% by weight alpha-lipoic acid and 9% by weight honokiol were found to be effective in promoting a significantly significant extension of neurites compared to control (culture A) and to the culture supplemented with growth factors (culture B), and especially also with respect to the culture additioned with a composition comprising 99.7% by weight alpha-lipoic acid and 0.3% by weight honokiol (culture C). It should be noted that the effect of the composition according to the invention, both in the proportions of 95.5% of alpha-lipoic acid and 4.5% honokiol, and of 91% alpha-lipoic acid and 9% honokiol, were found to be more significant than that obtained with the growth factor bFGF. The composition comprising 46% by weight alpha-lipoic acid and 54% by weight honokiol inhibited neurite outgrowth in culture F.

The compositions comprising alpha-lipoic acid alone or honokiol alone stimulated neurite growth in a negligible way. The result is a value not significantly different from that of the control composition.

FIG. 1 also shows that, after 7 days of cell culture, in cultures C, D and E (FIGS. 1*c*, 1*d* and 1*e*) neurons showed extended neurites that contained more prominent and dark neuronal somes compared to the control culture A (FIG. 1*a*), and were better, especially as regards the cultures D and E (FIGS. 1*d* and 1*e*), with respect to cultures B (FIG. 1*b*) respectively containing 40 ng ml$^{-1}$ of bFGF and cultures of individual alpha-lipoic acid (FIG. 1*d*) or honokiol (FIG. 1*h*).

The test results show that the compositions according to the invention have an undoubted and unpredictable effect on the differentiation of cortical neurons.

Example 2

Assessment of Neuronal Survival

Four primary cell cultures were prepared as described in Abe K et al. "*Effects of recombinant human basic fibroblast growth factor and its modified protein CS23 on survival of primary cultured neurons from various regions of fetal rat brain*", Jpn J Pharmacol 1990, 53 (2): 221-7. All operations were carried out under sterile conditions. The neuronal cells were separated from cerebral hemispheres of rat fetuses of 18 days (Japan SLC, Inc.) and suspended in 10% FBS/MEM, then seeded at 20,000 cells cm$^{-2}$ in poly-L-lysine plates.

After 24 hours, the culture medium was replaced with a serum-free medium, specific for the growth of neurons (Neurobasal Medium) supplemented with B27.

The procedure of the cell cultures was essentially the same as implemented in the example with NBM/B27 except that, as a culture medium free from serum, DMEM supplemented with N2 was used (Cestelli A et al. "*Formulation of a novel synthetic medium for selectively culturing rat CNS neurons*". Dev Brain Res 1985, 22.219); and also that plates had a cell density equal to 2×10$^5$ cm$^{-2}$.

Then, a culture (I) was used as the control culture.

A culture (L) was additioned with 99.7% by weight alpha-lipoic acid and 0.3% by weight honokiol to the concentration of 10 µM.

A culture (M) was additioned with 91% by weight alpha-lipoic acid and 9% by weight honokiol to the concentration of 10 µM.

A culture (N) was additioned with 46% by weight alpha-lipoic acid and 54% by weight honokiol to the concentration of 10 µM.

After being incubated for 3 days, the cells of the four cultures were fixed with 4% formaldehyde.

Neuronal survival was evaluated by the method of WST-8 H Tominaga et al. "*A water-soluble tetrazolium salt useful for colorimetric cell viability assay*", Anal Commun 1999, 36.47. This method uses a salt of 2-(2-methoxy-4-nitrophenyl)-3-(4-nitrophenyl)-5-(2.4-disolfofenil)-2H tetrazolium as a chromogen indicator to assess WST-8 cell viability, and produces results on cell viability that are in line with those obtained respectively with the MTT method using 3-(4,5-dimethyl-2-thiazolyl)-2,5-diphenyl-2H tetrazolium bromide, and with the tritiated thymidine uptake method.

Figure 2:
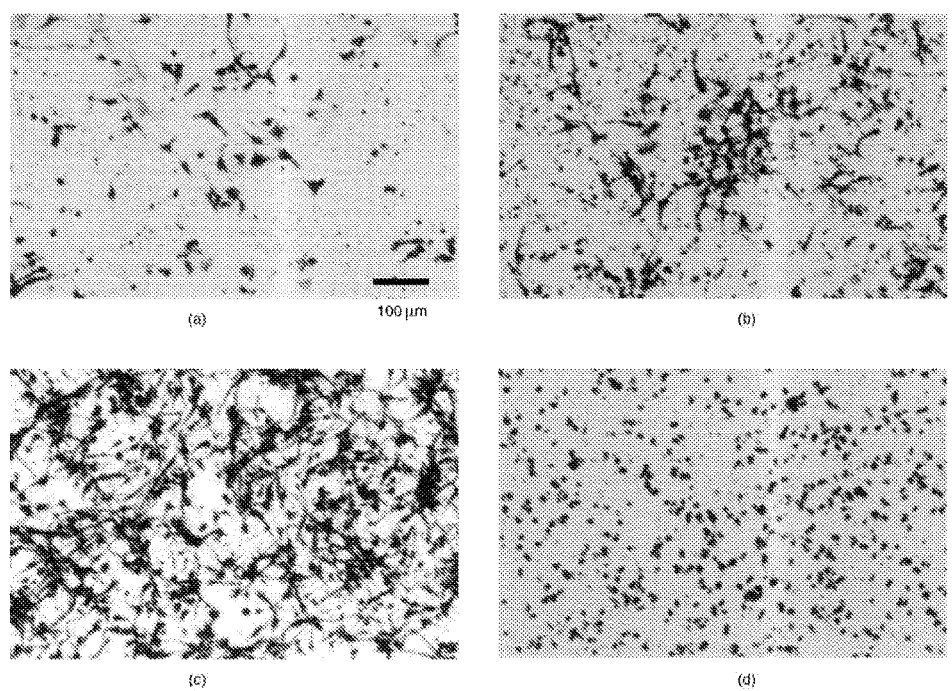
FIG. 2a shows a photograph of a primary cell culture of rat cortical neurons after 4 days in 0.5% EtOH.
FIG. 2b shows a photograph of a primary cell culture of rat cortical neurons after 4 days in 0.5% EtOH additioned with a 10 µM solution of 99.7% alpha-lipoic acid and 0.3% honokiol.
FIG. 2c shows a photograph of a primary cell culture of rat cortical neurons after 4 days in 0.5% EtOH additioned with a 10 µM solution of 91% alpha-lipoic acid and 9% honokiol.
FIG. 2d shows a photograph of a primary cell culture of rat cortical neurons after 4 days in 0.5% EtOH additioned with a 10 µM solution of 46% alpha-lipoic acid and 54% honokiol.

The results are shown both in Table 2, in which the values are expressed as average, and in FIG. 2. In Table 2, p indicates statistical significance and ns means "not significant".

TABLE 2

| Culture | % Absorbance at 450 nm with respect to control (culture I) |
|---|---|
| I | 100.0 |
| L | 106.0 (p = ns) |
| M | 143.1 (p < 0.001) |
| N | 29.7 (p < 0.001) |

Culture M has values that are significantly higher than the control I.

Reference culture I, in the absence of active principles, determined the survival of a small number of neurons. On the contrary, in culture M the presence of the compositions according to the present invention at the concentration of 10 μM, showed a high ability to grow and survive neurons.

Example 3

Four primary cell cultures were prepared as described in Example 2 (like in Abe K et al. "*Effects of recombinant human basic fibroblast growth factor and its modified protein CS23 on survival of primary cultured neurons from various regions of fetal rat brain*", Jpn. J. Pharmacol. 1990; 53 (2): 221-7).

Then, a culture (O) was used as the control culture.

A culture (P) was additioned with 91% by weight alpha-lipoic acid and 9% by weight honokiol to the overall concentration of 10 μM.

A culture (Q) was additioned with 91% by weight alpha-lipoic acid and 9% by weight honokiol to the concentration of 10 μM and 0.003 μM of Selenium.

A culture (R) was additioned with 91% by weight alpha-lipoic acid and 9% by weight honokiol to the concentration of 10 μM and 0.24 μM of gamma linolenic acid.

After being incubated for 3 days, the cells of the four cultures were fixed with 4% formaldehyde.

The survival of neurons was assessed by WST-8 reduction test (Tominaga et al., 1999). The results are shown in Table 3 in which the values are expressed as averages. Furthermore, p denotes statistical significance.

TABLE 3

| Culture | % Absorbance at 450 nm with respect to control (culture O) |
|---|---|
| O | 100.0 |
| P | 143.1 (p < 0.001) |
| Q | 178.9 (p < 0.001) |
| R | 176.5 (p < 0.001) |

The results reported in Table 3 show that, surprisingly, the compositions according to preferred embodiments of the invention, comprising selenium and/or gamma-linolenic acid are particularly effective in enhancing the survival of neuronal cultures. In particular, the compositions used in cultures Q and R are significantly more effective than those used for the cultivation of reference O and that used in culture P.

The invention claimed is:

1. A composition comprising alpha-lipoic acid, or a salt or complex thereof, and honokiol, in an amount sufficient to promote neurite extension and neuronal cell survival, wherein the weight amount of said honokiol is 1% to 30% with respect to the total weight of honokiol and alpha-lipoic acid in the composition.

2. The composition according to claim 1, wherein the weight amount of said honokiol is from 2% to 15% with respect to the total weight of honokiol and alpha-lipoic acid.

3. The composition according to claim 2, wherein the weight amount of said honokiol is from 3% to 10% with respect to the total weight of honokiol and alpha-lipoic acid.

4. The composition according to claim 1, further comprising gamma-linolenic acid or a salt or complex thereof.

5. The composition according to claim 4, wherein the amount of said gamma-linolenic acid is from 2% to 30% with respect to the total weight of honokiol and alpha-lipoic acid.

6. The composition according to claim 3, further comprising a physiologically acceptable source of selenium.

7. The composition according to claim 1, further comprising at least one component selected from the group consisting of vitamin C, vitamin E, and B vitamins.

8. A treatment of peripheral neuropathies, comprising administering an effective amount of a composition of claim 1 to a person in need thereof.

9. A dietary or pharmaceutical formulation for oral administration comprising a composition according to claim 1.

10. The formulation according to claim 9, in the form of tablets or capsules suitable for the daily administration of an amount from 200 mg to 1300 mg of alpha-lipoic acid and from 2.5 mg to 150 mg of honokiol.

11. The formulation according to claim 10 in the form of tablets or capsules suitable for the daily administration of an amount from 580 mg to 620 mg of alpha-lipoic acid and from 45 mg to 60 mg of honokiol, or suitable for the daily administration of an amount from 280 mg to 320 mg of alpha-lipoic acid and from 20 mg to 30 mg of honokiol.

12. The formulation according to claim 10, in the form of soft gelatin capsules suitable for the daily administration of an amount from 200 mg to 1300 mg of alpha-lipoic acid, from 2.5 mg to 150 mg of honokiol and from 10 mg to 300 mg of gamma-linolenic acid or a salt or complex thereof.

13. The formulation according to claim 11, in the form of soft gelatin capsules suitable for the daily administration of an amount from 580 mg to 620 mg of alpha-lipoic acid, of an amount from 45 mg to 60 mg of honokiol and from 125 mg to 140 mg of gamma-linolenic acid or suitable for the daily administration of an amount from 280 mg to 320 mg of alpha-lipoic acid, of an amount from 20 mg to 30 mg of honokiol and from 60 mg to 70 mg of gamma-linolenic acid.

* * * * *